(12) United States Patent
Neely et al.

(10) Patent No.: US 6,998,164 B2
(45) Date of Patent: Feb. 14, 2006

(54) CONTROLLED LOFT AND DENSITY NONWOVEN WEBS AND METHOD FOR PRODUCING SAME

(75) Inventors: James Richard Neely, Alpharetta, GA (US); Edward Jason White, Mauldin, SC (US); Kurtis Lee Brown, Alpharetta, GA (US); John Herbert Conrad, Alpharetta, GA (US); Richard Wallace Hoefer, Boise, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/463,945

(22) Filed: Jun. 18, 2003

(65) Prior Publication Data

US 2003/0213109 A1  Nov. 20, 2003

Related U.S. Application Data

(62) Division of application No. 09/537,564, filed on Mar. 30, 2000, now Pat. No. 6,588,080.

(60) Provisional application No. 60/132,031, filed on Apr. 30, 1999.

(51) Int. Cl.
*B32B 3/26* (2006.01)
*B32B 33/00* (2006.01)

(52) U.S. Cl. ............................. 428/86; 428/92; 428/93

(58) Field of Classification Search ................ 428/175, 428/181–183
See application file for complete search history.

(56) References Cited

U.S. PATENT DOCUMENTS

| | | |
|---|---|---|
| 255,381 A | 3/1882 | Doubleday |
| 2,331,146 A | 10/1943 | Slayter |
| 2,336,743 A | 12/1943 | Manning |
| 2,336,744 A | 12/1943 | Manning |
| 2,336,745 A | 12/1943 | Manning |
| 2,510,229 A | 6/1950 | Joa |
| 2,886,877 A | 5/1959 | Frickert et al. |
| 2,931,091 A | 4/1960 | Breen |
| 2,975,470 A | 3/1961 | Snelson et al. |
| 3,042,991 A | 7/1962 | Rona |
| 3,081,207 A | 3/1963 | Fox |
| 3,086,253 A | 4/1963 | Joa |
| 3,202,743 A | 8/1965 | Elmendorf |
| 3,368,934 A | 2/1968 | Vosburgh, Sr. |
| 3,481,005 A | 12/1969 | Owens et al. |
| 3,589,956 A | 6/1971 | Kranz et al. |
| 3,665,922 A | 5/1972 | Skora |
| 3,707,746 A * | 1/1973 | Summers ..................... 28/104 |

(Continued)

FOREIGN PATENT DOCUMENTS

CZ  235 494  11/1986

(Continued)

OTHER PUBLICATIONS

Radko Krema et al.: *What's New In Highloft Production?*, Nonwovens Industry, 74-78, Oct. 1997.

Primary Examiner—Cheryl A. Juska
Assistant Examiner—Jenna-Leigh Befumo
(74) Attorney, Agent, or Firm—Pauley Petersen & Erickson

(57) ABSTRACT

A lofty, nonwoven material having a nonwoven web having a plurality of substantially continuous fibers oriented in a z-direction of the nonwoven web and a method for producing the lofty, nonwoven material from as-formed z-direction fibers. The method is fast, having no mechanical manipulation of the fibers to slow it down, easily adjustable and allows for in-line processing. The material can be varied from preponderantly open to preponderantly closed in its web structure.

4 Claims, 5 Drawing Sheets

U.S. PATENT DOCUMENTS

| | | |
|---|---|---|
| 3,738,884 A | 6/1973 | Soehngen |
| 3,769,115 A | 10/1973 | Rasmussen et al. |
| 3,802,817 A | 4/1974 | Matsuki et al. |
| 3,849,241 A | 11/1974 | Butin et al. |
| 3,972,092 A | 8/1976 | Wood |
| 4,071,925 A | 2/1978 | Folk |
| 4,089,720 A | 5/1978 | Haley |
| 4,100,324 A | 7/1978 | Anderson et al. |
| 4,102,963 A | 7/1978 | Wood |
| 4,111,733 A | 9/1978 | Periers |
| 4,340,563 A | 7/1982 | Appel et al. |
| 4,357,379 A | 11/1982 | Sloan et al. |
| 4,434,205 A | 2/1984 | Fujii et al. |
| 4,440,597 A | 4/1984 | Wells et al. |
| 4,488,928 A | 12/1984 | Ali Khan et al. |
| 4,548,856 A | 10/1985 | Ali Khan et al. |
| 4,582,666 A | 4/1986 | Kenworthy et al. |
| 4,590,114 A | 5/1986 | Holtman |
| 4,624,819 A | 11/1986 | Hartog et al. |
| 4,701,365 A | 10/1987 | Iwasaki |
| 4,741,941 A | 5/1988 | Englebert et al. |
| 4,818,464 A | 4/1989 | Lau |
| 4,837,067 A | 6/1989 | Carey, Jr. et al. |
| 4,908,175 A | 3/1990 | Angstadt |
| 4,955,999 A | 9/1990 | Schaefer et al. |
| 5,032,122 A * | 7/1991 | Noel et al. .................. 604/391 |
| 5,071,615 A | 12/1991 | Ranzen |
| 5,093,069 A | 3/1992 | Mellem et al. |
| 5,108,827 A | 4/1992 | Gessner |
| 5,167,740 A | 12/1992 | Michaelis et al. |
| 5,198,057 A | 3/1993 | Newkirk et al. |
| 5,227,107 A | 7/1993 | Dickenson et al. |
| 5,261,146 A | 11/1993 | Belliot |
| 5,270,107 A | 12/1993 | Gessner |
| 5,366,793 A | 11/1994 | Fitts, Jr. et al. |
| 5,382,400 A | 1/1995 | Pike et al. |
| 5,500,295 A | 3/1996 | Halm et al. |
| 5,558,924 A | 9/1996 | Chien et al. |
| 5,620,545 A | 4/1997 | Braun et al. |
| 5,702,801 A | 12/1997 | Chien |
| 5,705,249 A | 1/1998 | Takai et al. |
| 5,707,468 A | 1/1998 | Arnold et al. |
| 5,725,734 A | 3/1998 | Herman et al. |
| 5,792,404 A | 8/1998 | Cree et al. |
| 5,814,390 A | 9/1998 | Stokes et al. |
| 5,888,607 A * | 3/1999 | Seth et al. .................... 428/92 |
| 5,932,316 A | 8/1999 | Cree et al. |
| 2003/0022584 A1 * | 1/2003 | Latimer et al. ............. 442/414 |

FOREIGN PATENT DOCUMENTS

| | | |
|---|---|---|
| CZ | 263 075 | 1/1990 |
| EP | 137 644 | 4/1985 |
| EP | 350 627 | 9/1994 |
| EP | 516 964 | 11/1996 |
| EP | 765 616 | 4/1997 |
| EP | 673 314 | 9/1998 |
| EP | 696 333 | 3/1999 |
| GB | 2 063 321 | 6/1981 |
| GB | 2 267 100 | 11/1993 |

* cited by examiner

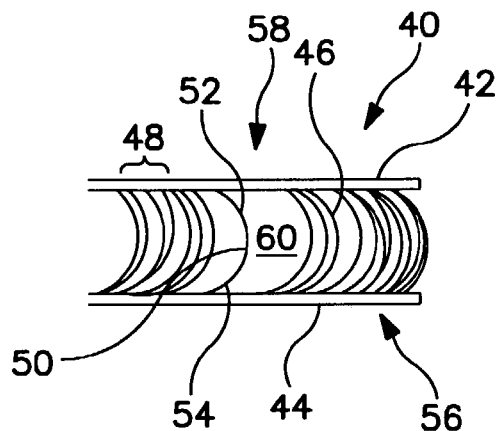
FIG. 5
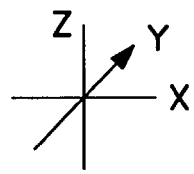
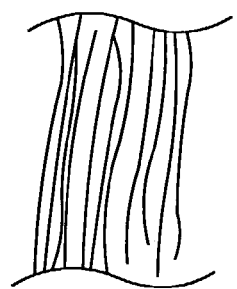
FIG. 6
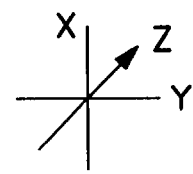
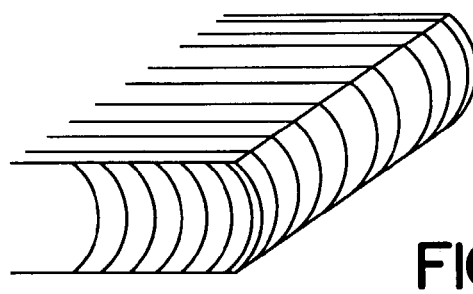
FIG. 7
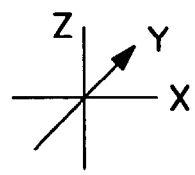

CONTROLLED LOFT AND DENSITY NONWOVEN WEBS AND METHOD FOR PRODUCING SAME

This application is a divisional application of U.S. patent application Ser. No. 09/537,564, filed 30 Mar. 2000 now U.S. Pat. No. 6,588,080, published Jul. 8, 2003.

BACKGROUND OF THE INVENTION

1. Field of the Invention

This invention relates to a lofty, nonwoven material produced from continuous fibers in which the lofty character of the nonwoven material is the result of the fibers comprising the web being oriented in a z-direction, that is outside of the plane of the orientation of the web, of the nonwoven material. These materials are particularly suitable for use in a broad range of applications including fluid management (surge), air and liquid filtration, acoustic and thermal insulation, packing material, absorbents, and cleaning materials. More particularly, these materials are suitable for use as surge, spacer layers, filtration materials and absorbent layers in personal care absorbent products including disposable diapers, incontinence garments, and feminine care products such as sanitary pads and napkins, and in face masks, surgical gowns, sterile wraps and surgical drapes. In addition, this invention relates to methods for producing such lofty, nonwoven materials.

2. Discussion of Related Art

Absorbent personal care articles such as sanitary pads and napkins, disposable diapers, incontinent-care pads and the like are widely used, and much effort has been made to improve their effectiveness and functionality. These articles generally include a liquid absorbent material backed by a liquid-impervious barrier sheet. To enhance the sense of comfort, the absorbent material has a facing of a material which masks at least the body-facing surface of the product. The purpose of this cover material is to help structurally contain the absorbent material and to protect the wearer from continuous direct contact with moisture from previously wetted absorbent material. The cover material is typically of relatively low basis weight nonwoven fabric. Improved product performance has been obtained in these products through the incorporation of a surge management material disposed between the cover material and the absorbent material. The surge management material is made from a relatively high basis weight, low density, that is, thick, nonwoven web material.

In nonwoven webs, the fibers comprising the web are generally oriented in the x-y plane of the web and the resulting nonwoven web material is relatively thin, that is lacking in loft or significant thickness. Loft or thickness in a nonwoven web suitable for use in personal care absorbent articles promotes comfort (softness) to the user, surge management and fluid distribution to adjacent layers.

In order to impart loft or thickness to a nonwoven web, it is generally desirable that at least a portion of the fibers comprising the web be oriented in the z-direction. Conventionally, such lofty nonwoven webs are produced using staple fibers. See, for example, U.S. Pat. No. 4,837,067 which teaches a nonwoven thermal insulating batt comprising structural staple fibers and bonding staple fibers which are entangled and substantially parallel to the faces of the batt at the face portions and substantially perpendicular to the faces of the batt, and U.S. Pat. No. 4,590,114 which teaches a batt including a major percent of thermo-mechanical wood pulp fibers stabilized by the inclusion of a minor percent of thermoplastic fibers including staple length thermoplastic fibers. Alternatively, conventional high loft forming processes rely on pre-forming processes such as fiber crimp formed on a flat wire or drum, and post-forming processes such as creping or pleating of the formed web.

SUMMARY OF THE INVENTION

In contradistinction to the known art, the present invention does not first form a web of material and pleat it. Rather, fibers are looped, or bent, on themselves without being first being formed into a material web. These fiber level loops, running between the major surfaces of the resultant web, are aggregated in the cross machine direction to form structures running in the cross machine direction which are herein sometimes called "waves" or "folds" to distinguish them from "pleats" which refer to structures in preformed web or mesh material that has been folded on itself.

Accordingly, it is one object of this invention to provide a high loft, low density nonwoven web material comprising substantially continuous fibers as opposed to staple fibers traditionally used in the manufacture of such nonwoven materials.

This and other objects of this invention are addressed by a lofty, nonwoven material comprising a nonwoven web comprising a plurality of substantially continuous fibers, which may be crimped or linear, oriented in a z-direction of the nonwoven web. The substantially continuous fibers are preferably spunbond and/or meltblown. In accordance with one embodiment of this invention, a support structure may be attached to at least one face of the nonwoven web, thereby providing strength to the high loft nonwoven web. This laminate structure provides support for the high loft structure, strength for winding, converting, etc., and a boundary layer to either enhance or retard fluid flow into the lofty absorbent structure in products such as disposable diapers, incontinence garments, and absorbent feminine care products including sanitary pads and napkins.

The lofty, nonwoven material of this invention is produced in accordance with one embodiment of this invention by a process in which a plurality of substantially continuous fibers are directed into a variable nip, resulting in bending of the fibers and formation of a nonwoven web. Within the nip the fibers may be subjected to a vacuum from both sides of the nip, either equally or differentially, producing a lofty, nonwoven web having a plurality of the substantially continuous fibers oriented in a z-direction.

In accordance with another embodiment of this invention, the lofty, nonwoven material is produced by directing a plurality of continuous, substantially linear, filament fibers through a slot formed by two opposed surfaces whereby the substantially continuous fibers bend from contact with the two opposed surfaces, which may be differential speeds or vacuum, or both, thereby forming a lofty, nonwoven web having a plurality of as-formed z-direction fibers.

BRIEF DESCRIPTION OF THE DRAWINGS

These and other objects and features of this invention will be better understood from the following detailed description taken in conjunction with the drawings wherein:

FIGS. 5–7 illustrate a material made according to the method of FIG. 2 with equal speed on the opposing surfaces.

DETAILED DESCRIPTION OF THE PRESENTLY PREFERRED EMBODIMENTS

Definitions

As used herein, the term "nonwoven web" or "nonwoven material" means a web having a structure of individual fibers, filaments or threads which are interlaid, but not in a regular or identifiable manner, such as in a knitted fabric and films that have been fibrillated. Nonwoven webs or materials have been formed from many processes such as, for example, meltblowing processes, spunbonding processes, and bonded carded web processes. The basis weight of nonwoven webs or materials is usually expressed in ounces of material per square yard (osy) or grams per square meter (gsm), and the fiber diameters usable are usually expressed in microns. (Note that to convert from osy to gsm, multiply osy by 33.91.)

Figure 3A:
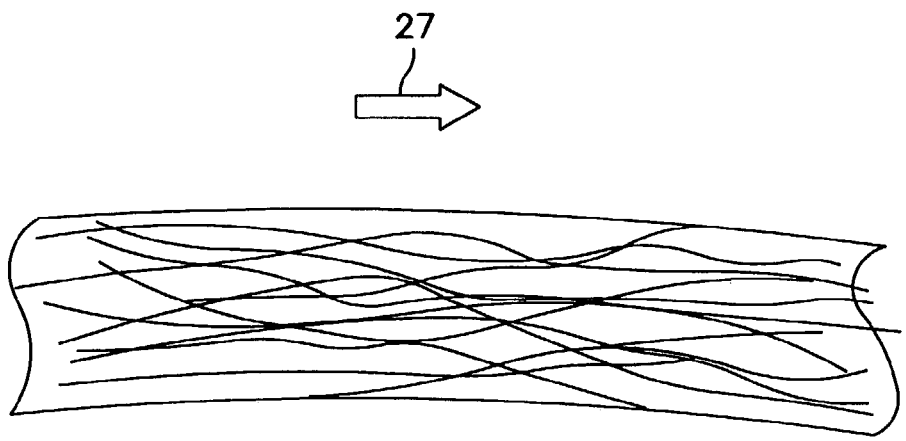
FIGS. 3A and 3B are diagrammatic representations of a conventional nonwoven web and a high loft nonwoven web in accordance with this invention, respectively.
Figure 3B:
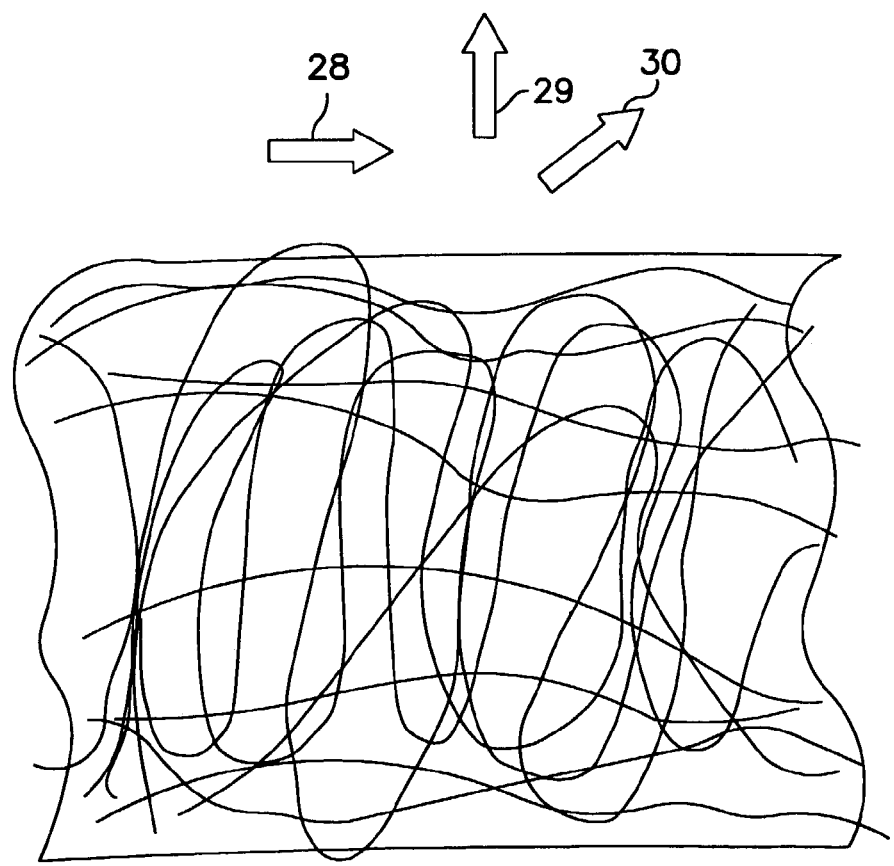

As used herein, the term "z-direction" refers to fibers disposed outside of the plane of orientation of a web. FIG. 3A is a diagram showing a nonwoven web without z-direction fibers. That is, all of the fibers are generally oriented in the direction indicated by arrow 27. By comparison, FIG. 3B is a diagram showing a nonwoven web having z-direction fibers in accordance with this invention. That is, in addition to fibers oriented in the direction of arrow 28, fibers are also oriented in the direction of arrows 29 and 30. The term "as formed z-direction fibers" as used herein refers to fibers that become oriented in the z-direction during forming of the nonwoven web as distinguished from fibers having a z-direction component resulting from post-forming processing of the nonwoven web, such as in the case of mechanically crimped or creped nonwoven webs.

As used herein, the term "spunbond fibers" refers to small diameter fibers which are formed by extruding molten thermoplastic material as filaments from a plurality of fine, usually circular capillaries of a spinneret as taught, for example, by U.S. Pat. No. 4,340,563 to Appel et al. and U.S. Pat. No. 3,802,817 to Matsuki et al.

As used herein, the term "meltblown fibers" refers to fibers formed by extruding a molten thermoplastic material through a plurality of fine, usually circular, die capillaries as molten threads or filaments into converging high velocity gas streams (for example, airstreams) which attenuate the filaments of molten thermoplastic material to reduce their diameter, which may be to microfiber diameter. Such a process is disclosed, for example, by U.S. Pat. No. 3,849,241 to Butin.

As used herein, the term "microfibers" refers to small diameter fibers having an average diameter not greater than about 75 microns, for example, having an average diameter of from about 0.5 microns to about 50 microns, or more particularly, having an average diameter of from about 2 microns to about 40 microns.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" also includes all possible geometric configurations of the material. These configurations include, but are not limited to, isotactic, syndiotactic, atactic and random symmetries.

As used herein, the term "personal care absorbent article" means disposable diapers, training pants, absorbent underpants, adult incontinence products, feminine hygiene products and the like.

As used herein, the term "homofilament" refers to a fiber formed from only one polymer. This is not meant to exclude fibers formed from one polymer to which small amounts of additives have been added for coloration, anti-static properties, lubrication, hydrophilicity, etc.

As used herein, the term "bicomponent fibers" refers to fibers which have been formed from at least two polymers extruded from separate extruders but spun together to form one fiber. Bicomponent fibers are also sometimes referred to as conjugate fibers or multicomponent fibers. Bicomponent fibers are taught by U.S. Pat. No. 5,382,400 to Pike et al.

As used herein, the term "biconstituent fibers" refers to fibers which have been formed from at least two polymers extruded from the same extruder as a blend. The tern "blend" is defined below. Biconstituent fibers are sometimes also referred to as multiconstituent fibers. Fibers of this general type are discussed in, for example, U.S. Pat. No. 5,108,827 to Gessner. As used herein, the term "blend" means a mixture of two or more polymers.

As used herein, the term "substantially continuous fibers" refers to fibers, including without limitation, spunbond and meltblown fibers, which are not cut from their original length prior to being formed into a nonwoven web or fabric. Substantially continuous fibers may have average lengths ranging from greater than about 15 centimeters to more than one meter, and up to the length of the web or fabric being formed. The definition of "substantially continuous fibers" includes fibers which are not cut prior to being formed into a non woven web or fabric, but which are later cut when the nonwoven web or fabric is cut, and fibers which are substantially linear or crimped.

The term "staple fibers" means fibers which are natural or cut from a manufactured filament prior to forming into a web, and which have an average length ranging from about 0.1–15 centimeters, more commonly about 0.2–7 centimeters.

As used herein, the term "through-air bonding" or "TAB" means the process of bonding a nonwoven, for example, a bicomponent fiber web in which air which is sufficiently hot to melt one of the polymers of which the fibers of the web are made is forced through the web.

Potential applications for the nonwoven web of this invention include personal care absorbent articles such as diapers, training pants, incontinence garments, feminine care products including sanitary pads and napkins, all surge materials, loop for look and loop, air filtration, liquid filtration, body scrub pads, oil sorb, baby wipes, industrial wipes, insulation and packaging material. In the case of filtration materials, the method of this invention greatly increases the surface area and volume available for filtration. In addition, the method of this invention may be suitable for producing coforms or composite materials incorporating high loft surge/pulp/superabsorbent material. And, for a Continuous roll of diapers, a composite material made by the present invention could be produced by ridging or ruffling a high loft surge/pulp/superabsorbent material laminate and placing it in between an outer cover and a liner, which would produce a laminate with all of the components of a diaper in a single step, which could be wound up and cut and placed later on converting machines.

The lofty or high loft nonwoven material of this invention comprises a nonwoven web comprising a plurality of substantially continuous fibers oriented in a z-direction of the nonwoven web. The substantially continuous fibers preferably are drawn in spunbond or meltblown processes. The substantially continuous fibers are preferably formed with polymers selected from the group consisting of polyolefins, polyamides, polyesters, polycarbonates, polystyrenes, thermoplastic elastomers, fluoropolymers, vinyl polymers, and blends and copolymers thereof. Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate, polytrimethyl terephthalate, polylactic acid and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may have thermoplastic elastomers blended therein.

In accordance with one preferred embodiment of this invention, the substantially continuous fibers are bicomponent fibers. Particularly suitable polymers for forming the structural component of suitable bicomponent fibers include polypropylene and copolymers of polypropylene and ethylene, and particularly suitable polymers for the adhesive component of the bicomponent fibers includes polyethylene, more particularly linear low density polyethylene, and high density polyethylene. In addition, the adhesive component may contain additives for enhancing the crimpability and/or lowering the bonding temperature of the fibers, and enhancing the abrasion resistance, strength and softness of the resulting webs. The nonwoven web of the material of this invention has a basis weight in the range of about 0.25 osy to about 50 osy. To enhance the absorption characteristics of the nonwoven material, in accordance with one embodiment of this invention, the nonwoven web comprises an absorbent, for example, superabsorbent particles as a coform.

In accordance with one embodiment of this invention, a support structure is attached to at least one face of the nonwoven web so as to provide strength thereto. The resulting laminate structure provides support for the high loft structure, strength for winding, converting, etc., and a boundary layer to either enhance or retard fluid flow into the lofty absorbent structure. The support structure may include spunbond webs of various types including liners, perforated, micro-fiber, creped, etc., spunbond-meltblown-spunbond (SMS), meltblown, and/or films.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. No. 4,818,464 to Lau.

Figure 1:
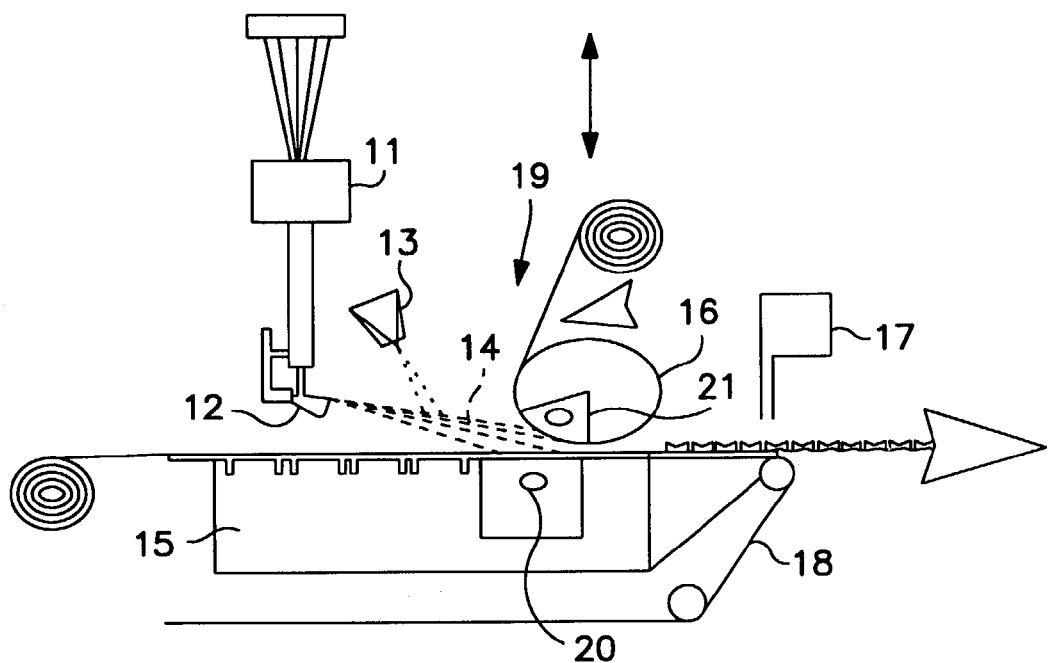
FIG. 1 is a diagram of a process for producing a lofty, nonwoven material in accordance with one embodiment of this invention.
Figure 4:
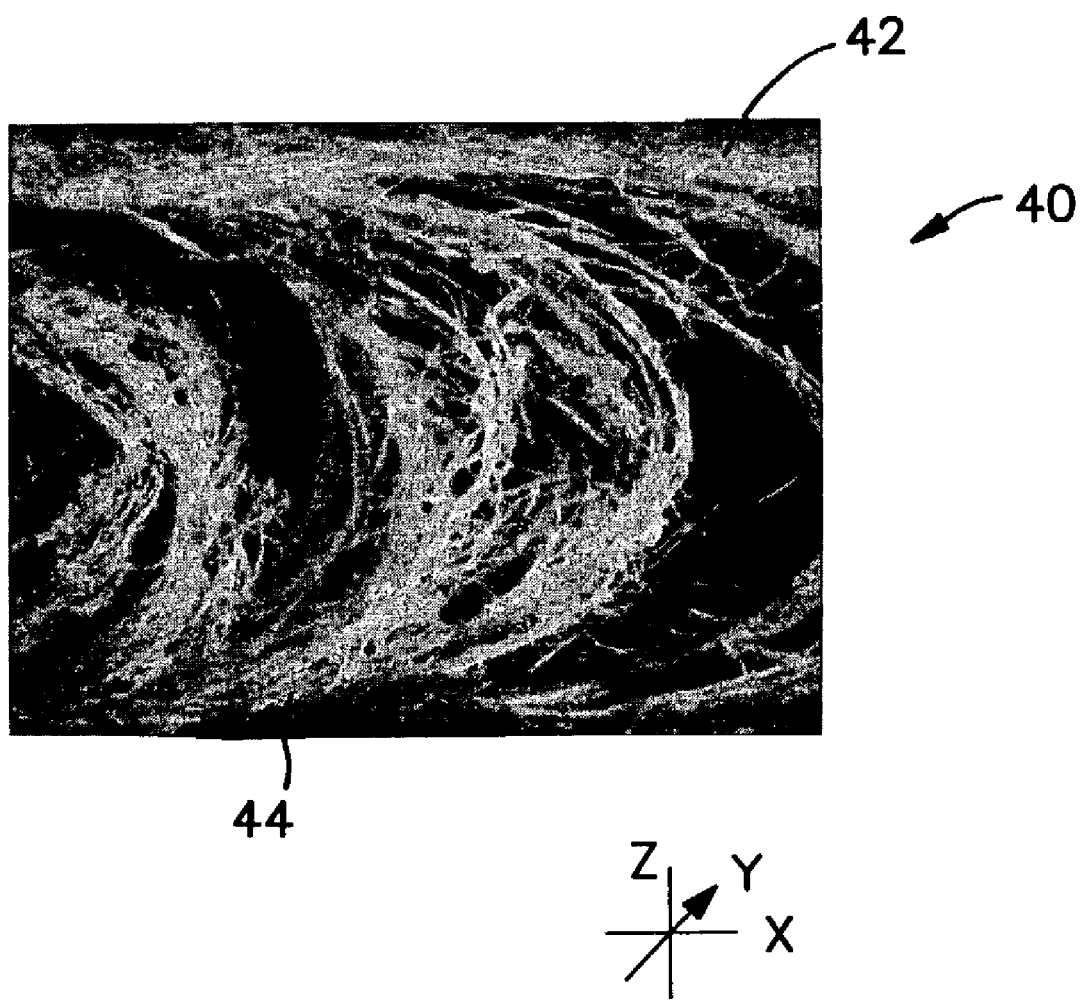
FIG. 4 is a photograph of a side view of a high loft nonwoven web produced in accordance with the method of this invention.

In a method for producing a lofty, nonwoven material in accordance with one embodiment of this invention, FIG. 1, a plurality of substantially continuous fibers are conveyed into a variable nip 19, that is a nip in which one of the elements forming the nip is adjustable, thereby enabling adjustment of the size of the nip in which the fibers are subjected to a vacuum from both sides of the nip, resulting in a lofty, nonwoven web having a plurality of the substantially continuous fibers oriented in a z-direction. Such a lofty, nonwoven web is shown in FIG. 4 in which the individual fibers comprising the web can be seen.

In accordance with the embodiment shown in FIG. 1, a plurality of substantially continuous fibers 14 are generated by a fiber forming unit 11 and are deflected by deflector 12 directly into a variable nip 19 formed by drum former 16 and forming surface 18. In accordance with the embodiment shown, the nip is varied by vertically adjusting drum former 16. Varying the nip in this fashion allows control over the density and loft of the nonwoven web. Within drum former 16 disposed above the nonwoven web, forming box 15 disposed below the forming surface 18, are means for subjecting the substantially continuous fibers 14 to a vacuum as the web passes through variable nip 19. The nonwoven web is thus formed in the variable nip 19, as opposed to upstream of the nip on a forming surface, is a high loft nonwoven web. Loft in the nonwoven web as it passes through the variable nip can be maintained by application of the vacuum to both sides of the web. In accordance with one embodiment of this invention, the resulting lofty, nonwoven web is subjected to treatment by a hot air knife 17 for the purpose of increasing the integrity of the nonwoven web. A hot air knife is used to bond the individual polymer fibers together at various locations so that the web has increased strength and structural integrity for subsequent treatments such as passage through a through-air bonding unit. A conventional hot air knife includes a mandrel with a slot that blows a jet of hot air onto the nonwoven web surface. Such hot air knives are taught, for example, by U.S. Pat. No. 5,707,468 to Arnold et al. Alternatively, the nonwoven web may be set by an adhesive sprayed onto the fibers prior to entering variable nip 19 by adhesive system 13, or by a combination thereof, e.g., a thermally activated adhesive.

Although shown as a combination of drum former 16 and forming surface 18, it will be apparent to those skilled in the art that variable nip 19 may be formed by other means, such as two drum formers, two opposed moving belts, etc.

In order to vary the 3-dimensional structure of the nonwoven web for a given fiber, the relative speeds of the drum former 16 and moving forming surface 18, as well as the height of the nip, and amount of vacuum may be varied. In accordance with one preferred embodiment of this invention, the speed of rotation of drum former 16 corresponds to the speed at which moving forming surface 18 is traveling. In accordance with another preferred embodiment of this invention, the speed at which drum former 16 is rotating is different from the speed of travel of moving forming surface 18. After forming in variable nip 19, the nonwoven web is integrally fixed, i.e., its structure is set by a hot air knife, adhesive, a calender, through-air-bonding unit, or the like and without laminate additions.

In accordance with one preferred embodiment of this invention, laminate structures are produced by unwinding and/or alternately producing and introducing one or more fabrics to be formed upon the web of the present invention. By either unwinding onto drum former 16 and/or web forming surface 18, applying adhesive in one or more possible places, and forming the lofty, nonwoven web as described hereinabove, a multi-layer laminate structure can be produced.

Figure 2:
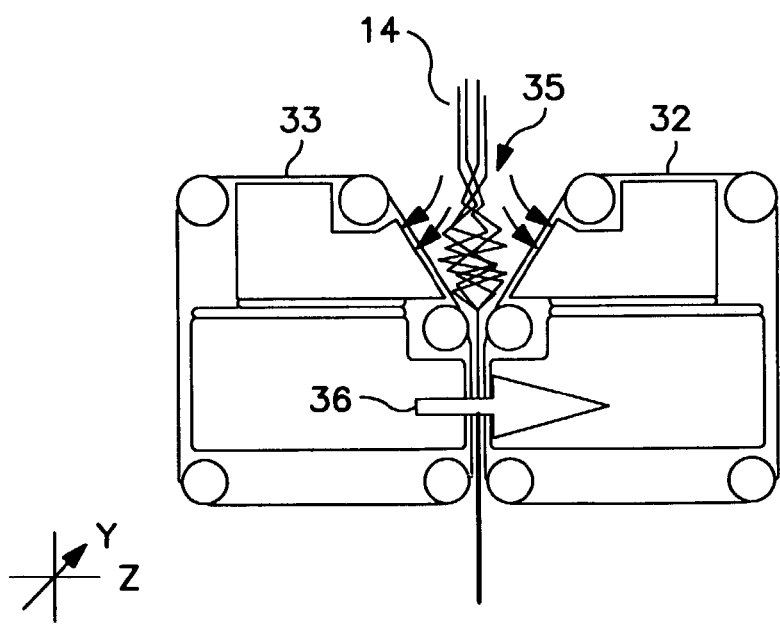
FIG. 2 is a diagram of another process for producing a lofty, nonwoven material in accordance with another embodiment of this invention.

FIG. 2 is a diagram showing an alternative method for producing a lofty, nonwoven material in accordance with this invention. In the embodiment shown in FIG. 2, substantially continuous fibers 14 are directed in a first direction, in this instance vertically downward, through slot 35 formed by two opposed surfaces, such as foraminous or perforate, forming wires 32, 33, whereby the substantially continuous fibers bend from contact with the two opposed surfaces, forming a lofty, nonwoven web having a plurality of as-formed z-direction fibers. After passing through slot 35, the resulting lofty, nonwoven web may be passed through a calender unit or some other downstream apparatus such as a through-air bonder for further processing. Alternatively, as shown in FIG. 2, where slot 35 is formed by the two foraminous wires 32, 33, the high loft nonwoven web may be subjected to through-air bonding, as at arrow 36, as the web passes through slot 35, thereby enabling the web to be formed in a single step.

The loft and density of the nonwoven web produced in accordance with the method of this invention is defined in part by the distance between the two opposed surfaces 32, 33. The density of the nonwoven web may be controlled by adjustment of the speed at which the nonwoven web passes through slot 35 and/or by varying the width of slot 35. Slot 35 may be a fixed plate slot, but the dual wire system shown in FIG. 2 is considered to be a more efficient method of web forming. Typically, adjustment of the distance between opposed surfaces forming the nip or slot, the speed at which the material passes through the nip or slot, and the relative speed of the moving surfaces forming the nip or slot and amount and direction of applied vacuum, are necessary to produce a nonwoven web with given characteristics. The forming nip or slot may also have parallel, or converging, or a series of converging and expanding slots. Adjustment of any or all of these factors may result in great variations of web characteristics.

As stated above, spunbond and meltblown fibers can be used to produce the high loft nonwoven web of this invention. Single component (homofilament), bicomponent and biconstituent fibers can be used. Bicomponent fibers are preferred in accordance with one embodiment of this invention because they have the advantage that thermal bonding fiber crimp can be used to enhance lofty material properties. The fibers can also be either quenched (rapidly cooled), in which case the outer surface of the fibers is solidified, or unquenched in which case the outer surface of the fibers remains tacky. Unquenched fibers have the advantage of bonding to each other without a further bonding requirement. Thermoplastic fibers can be through-air bonded in a stuffed through-air bonder unit symbolically shown as arrow 36 in FIG. 2, thereby providing a one-step forming/bonding process. Other types of bonding, such as bonding rolls, may be placed after the stuffed through-air-bonder unit for material consolidation, including point-bonding, hydro-entangling, or needle punching.

Referencing FIGS. 4–7 a nonwoven material 40 made according to the method of FIG. 2 has first and second major surfaces 42, 44 in the plane of the web, i.e., generally parallel to the XY plane, and spaced apart in the Z direction. The continuous fibers, e.g., 46, are folded to form loops, e.g., 48, whose z-direction termini are fused into the first and second major surfaces 42, 44. Referencing FIG. 5 the major surfaces are substantially flat or planar, i.e., within the limits of manufacturing and material tolerances, and may be preponderantly open or closed, i.e., majority air or fiber, respectively, dependent upon process parameters of belt speed, belt speed differential, type of fiber, vacuum applied, etc. The loops 48, generally form a succession of "U"-shaped waveforms with the bight 50 of the "U" protruding in the machine, or X axis, direction and midway between the first and second major surfaces 42, 44. The legs 52, 54 of the "U" extend retrograde of the bight 50 towards the major surfaces 42, 44. The loops aggregate in the cross machine direction, or Y axis to form waves or folds running, or extending, in the cross machine direction and being z-direction oriented to add loft to the nonwoven material. The periodicity of the waveforms may be regular or random and recurrent as seen in FIG. 5 where the loops are alternately more densely 56 and less densely 58 packed along the machine direction. With this embodiment of low density material definite open channels 60 may be seen between the waves.

The fabric of FIGS. 4–7 was made using no speed differential between the moving surfaces 32, 33 and with no vacuum applied to opposite sides of the slot 35.

Figure 8:
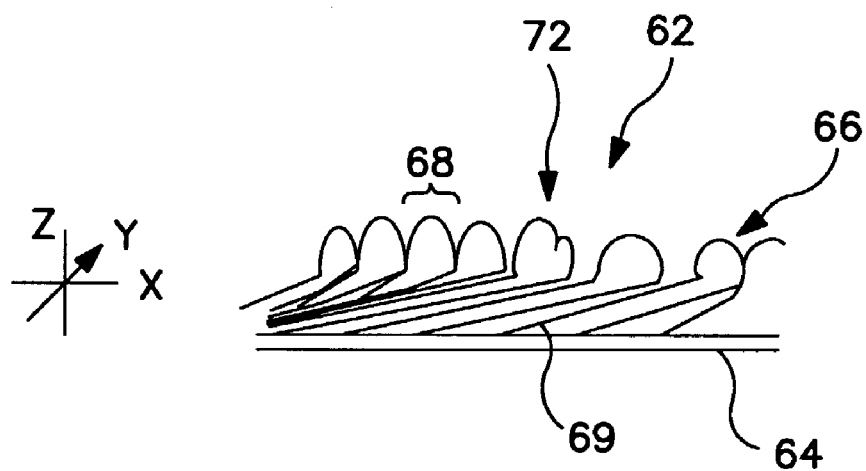
FIGS. 8–10 illustrate a material made according to the method of FIG. 2 with differential speed on the opposing surfaces.
Figure 9:
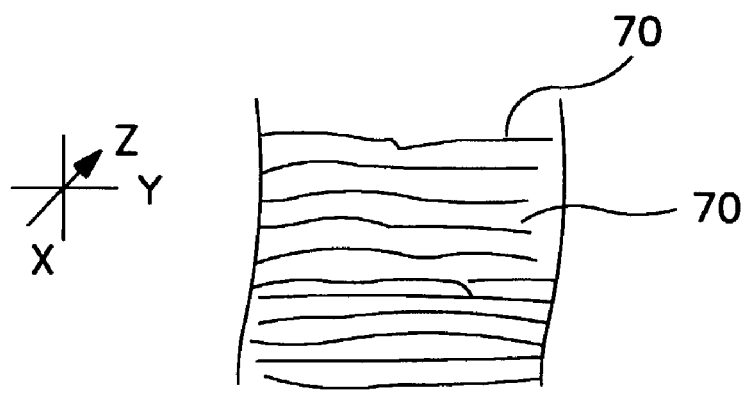
Figure 10:

As seen in FIGS. 8–10, a lofty nonwoven material 62 has first major surface 64 which is substantially flat or planar, and a second major surface 66 which is ridged or waved. The fiber loops, e.g., 68 have termini 69 fused into the first major surface 64, but are not fused and therefore protrude in the Z direction at the second major surface 66. The termini extend retrograde of the loops, e.g., 68, owing to the differential speed of the forming surfaces, or wires 32, 33. The loops aggregate in the cross machine direction to form serial successive waveforms, collectively 70 as in FIG. 9. In this case the first major surface 64 was formed on the slower moving of the opposing surfaces. If vacuum is differentially applied the first major Surface would receive the greater vacuum. In terms of gross morphology, the first major surface 64 is substantially flat and preponderantly closed in the given example. The waveforms are preponderantly regular in periodicity and length along the cross machine direction. The waves 70 at the second major surface may be crenulate as at 72 depending on the height of slot 35, type of fiber used and other factors. Of course, as stated above, the gross morphology may be easily altered by adjustment of a number of factors within the manufacturing process.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A lofted web of nonwoven material comprising: a plurality of substantially continuous fibers, the web having x, y and z directions, edges, and a first major surface in an x-y plane, with x being a machine direction, y being a cross machine direction and z being a loft direction;

the substantially continuous fibers oriented in the z-direction and folded to form loops;

the loops form a waved material with a train of waves spaced along the machine direction running from edge to edge in the cross direction and extending in the z-direction; and the first major surface is flat; and the web is integrally fixed with each wave being a substantially "U"-shaped wherein said U-shape has a bight protruding in the loft direction and the legs of the "U" are spaced along the machine direction and extend towards the first major surface and the legs of the "U" extending retrograde towards the first major surface.

2. A lofted web of nonwoven material comprising: a plurality of substantially continuous fibers, the web having x, y and z directions, edges, and a first major surface in an x-y plane, with x being a machine direction, y being a cross machine direction and z being a loft direction;
- the substantially continuous fibers oriented in the z-direction and folded to form loops;
- the loops form a waved material with a train of waves spaced along the machine direction running from edge to edge in the cross direction and extending in the z-direction; and
- the first major surface is flat; and
- the web is integrally fixed with each wave being a substantially "U"-shaped wherein said U-shape has a bight protruding in the loft direction and the legs of the "U" are spaced along the machine direction and extend towards the first major surface; and further including the legs of the "U" extending retrograde towards the first surface; and
- said material being made by a method for producing a lofty, nonwoven material comprising the steps of:
- directing a plurality of substantially continuous fibers into a nip; and
- subjecting said substantially continuous fibers to a vacuum from both sides of said nip, producing a lofty, nonwoven web having z-direction oriented fibers; and
- wherein said nip comprises two nip elements having a surface moving at different linear speeds in a machine direction.

3. A lofted web of nonwoven material comprising:
- a single layer formed from a plurality of substantially continuous fibers, the single layer having x, y and z directions, edges, and a first major surface in an x-y plane, with x being a machine direction, y being a cross machine direction and z being a loft direction;
- the substantially continuous fibers oriented in the z-direction and folded to form loops;
- the loops form a waved material with a train of waves spaced along the machine direction running from edge to edge in the cross direction and extending in the z-direction; and
- the first major surface is flat; and
- the single layer being integrally fixed with each wave being substantially "U"-shaped wherein said U-shape has a bight protruding in the loft direction and the legs of the "U" are spaced along the machine direction and extend towards the first major surface; and further including the legs of the "U" extending retrograde towards the first major surface.

4. A lofted web of nonwoven material comprising:
- a single layer formed from a plurality of substantially continuous fibers, the single layer having x, y and z directions, edges, and a first major surface in an x-y plane, with x being a machine direction, y being a cross machine direction and z being a loft direction;
- the substantially continuous fibers oriented in the z-direction and folded to form loops;
- the loops form a waved material with a train of waves spaced along the machine direction running from edge to edge in the cross direction and extending in the z-direction; and
- the first major surface is flat; and
- the single layer being integrally fixed with each wave being substantially "U"-shaped wherein said U-shaped has a bight protruding in the loft direction and the legs of the "U" are spaced along the machine direction and extend towards the first major surface; and further including the legs of the "U" extending retrograde towards the first surface; and
- made by a method for producing a lofty, nonwoven material comprising the steps of:
- directing a plurality of substantially continuous fibers into a nip; and
- subjecting said substantially continuous fibers to a vacuum from both sides of said nip, producing a lofty, single layer nonwoven web having z-direction oriented fibers; and
- wherein said nip comprises two nip elements having a surface moving at different linear speeds in a machine direction.

* * * * *